United States Patent
Morgan et al.

(10) Patent No.: US 6,692,726 B1
(45) Date of Patent: Feb. 17, 2004

(54) ENZYME CONTAINING ORAL COMPOSITION HAVING ENHANCED STABILITY

(75) Inventors: André M. Morgan, Plainsboro, NJ (US); Lori H. Szeles, Howell, NJ (US); Malcolm Williams, Piscataway, NJ (US); Susan M. Herles, Flemington, NJ (US); Chanda L. Macias, Somerset, NJ (US); Robert D'Ambrogio, Bound Brook, NJ (US); Thomas J. Boyd, Somerset, NJ (US); James G. Masters, Ringoes, NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 10/364,241

(22) Filed: Feb. 11, 2003

(51) Int. Cl.[7] .................. A61K 7/16; A61K 71/18; A61K 19/00; C07G 7/02
(52) U.S. Cl. .................. 424/50; 424/49; 424/54
(58) Field of Search .................. 424/50, 54

(56) References Cited

U.S. PATENT DOCUMENTS

| | | | | |
|---|---|---|---|---|
| 3,681,197 A | * | 8/1972 | Smith | 185/63 |
| 3,933,588 A | * | 1/1976 | Dworschack et al. | 435/179 |
| 5,437,856 A | * | 8/1995 | Lukacovic et al. | 424/50 |
| 5,560,905 A | * | 10/1996 | Lukacovic | 424/50 |
| 5,622,689 A | * | 4/1997 | Lukacovic | 424/50 |
| 5,801,226 A | * | 9/1998 | Cummins et al. | 530/388.2 |
| 5,827,505 A | * | 10/1998 | Hughes et al. | 424/49 |
| 5,849,271 A | * | 12/1998 | Lukacovic et al. | 424/50 |
| 6,187,295 B1 | * | 2/2001 | Glandorf et al. | 424/52 |
| 6,350,436 B1 | * | 2/2002 | Glandorf et al. | 424/52 |
| 6,511,654 B2 | * | 1/2003 | Ibsen et al. | 424/49 |
| 6,555,094 B1 | * | 4/2003 | Glandorf et al. | 424/52 |
| 6,589,562 B1 | * | 7/2003 | Shefer et al. | 424/490 |

* cited by examiner

Primary Examiner—Shep K. Rose
(74) Attorney, Agent, or Firm—Ellen K. Park

(57) ABSTRACT

An oral care composition having enhanced oral hygiene and antiplaque properties which comprises an orally acceptable vehicle containing a combination of an enzyme, cetylpyridinium chloride and a reducing agent.

30 Claims, No Drawings

ENZYME CONTAINING ORAL COMPOSITION HAVING ENHANCED STABILITY

BACKGROUND OF THE INVENTION

1. Field of the Invention

This invention relates generally to oral compositions for enhancing oral hygiene, and more particularly, to enzyme containing oral compositions having enhanced stability and antiplaque effectiveness.

2. The Prior Art

Oral compositions such as toothpastes, gels and mouth washes are designed to loosen and remove plaque in conjunction with a regular toothbrushing regimen. Dental plaque is present to some degree, in the form of a film, on virtually all dental surfaces. It is a byproduct of microbial growth, and comprises a dense microbial layer consisting of a mass of microorganisms embedded in a polysaccharide matrix. Plaque itself adheres firmly to dental surfaces and is removed only with difficulty even through a rigorous brushing regimen. Moreover, plaque rapidly reforms on the tooth surface after it is removed. Plaque may form on any part of the tooth surface, and is found particularly at the gingival margin, in cracks in the enamel, and on the surface of dental calculus. The danger associated with the formation of plaque on the teeth lies in the tendency of plaque to build up and eventually produce gingivitis, periodontitis and other types of periodontal disease, as well as dental caries and dental calculus.

It is known to the art to incorporate antimicrobial agents in oral compositions wherein these agents destroy or inhibit oral bacteria. Other agents are also incorporated in the oral composition to enhance the efficacy of the antimicrobial agents. For example, it is known to incorporate enzymes such as proteases in oral compositions, which enzymes disrupt or interfere with plaque formation and bacterial adhesion to tooth surfaces.

A problem encountered with commercially processed enzymes such as proteases is that they often contain a broad spectrum of undesirable by-products or impurities that are difficult to remove during manufacture. One such enzyme by-product is cellulase, an enzyme that catabolizes cellulose to simple sugars by hydrolysis of β (1–4) linkages.

Thickening agents conventionally used in oral compositions such as carboxymethyl cellulose, undergo degradation in the presence of cellulase enzymes which detrimentally affects the rheology of the dentifrice product. Thus, a means to inhibit the degradation of these thickeners by cellulase is a critical to obtaining stable enzyme containing oral care formulations.

Typical methods employed by the art for cellulase inhibition or isolation are not practical for use in the oral composition field. Treatments for cellulase inhibition such as salting out, heat treatment, or pH adjustment also compromise the activity of the enzymes. Classical methods of enzyme separation based on enzyme size, charge, solubility, and binding site are cost prohibitive and ineffective due to the similarities between certain cellulases and enzymes such as amylases. Inhibition of cellulase activity by treatment with heavy metals or heavy metal complexes such as mercury, silver and palladium chloride that bind to the enzyme active site are also unacceptable as these materials are toxic to humans and certainly cannot be used in an oral care product.

SUMMARY OF THE INVENTION

In accordance with the present invention it has been unexpectedly determined that a small but effective amount of cetyl pyridinum chloride and a reducing agent can provide enhanced stability and antiplaque efficacy in enzyme containing oral compositions.

DESCRIPTION OF THE PREFERRED EMBODIMENTS

Cetyl Pyridinum Chloride

Cetyl pyridinium chloride is incorporated in containing oral care compositions of the present invention at a concentration of about 0.005 to about 1.0% by weight and preferably about 0.50 to about 1.0% by weight of the oral care composition.

Enzymes

The enzymes useful in the practice of the present invention include carbohydrases such as glucoamylase and enzymes extracted from natural fruit products such as proteases which breakdown or hydrolyze proteins.

Glucoamylase is a saccharifying glucoamylase of *Aspergiullus niger* origin cultivated by fermentation. This enzyme can hydrolyze both the alpha-D-1,6 glucosidic branch points and the alpha-1,4 glucosidic bonds of glucosyl oligosaccharides. Additional carbohydrases useful in accordance with this invention are alpha and beta-amylase, dextranase and mutanase. Glucoamylase is a preferred enzyme and is incorporated in the oral composition of the present invention at a concentration of about 0.001 to 2% by weight and preferably about 0.01 to 0.55% by weight.

Protease enzymes useful in the practice of the present invention include those extracted from natural fruit products. The proteolytic enzymes are obtained from natural sources or by the action of microorganisms having a nitrogen source and a carbon source. Examples of proteolylic enzymes useful in the practice of the present invention include the naturally occurring enzymes papain (from papaya), bromelain (from pineapple), as well as serine proteases such as chymotrypsin. Additional enzymes include ficin and alcalase. Papain is a protease enzyme preferred for use in the practice of the present invention, the papain having an activity of 150 to 939 MCU per milligram as determined by the Milk Clot Assay Test of the Biddle Sawyer Group (see J. Biol. Chem., vol. 121, pages 737–745). The protease enzymes are included in the compositions of the present invention at a concentration of about 0.1 to about 3% by weight and preferably about 0.2 to about 2% by weight.

Enzymes which may beneficially be used in combination with the proteolytic enzymes and glucoamylase enzymes include carbohydrases such as, alpha-amylase, beta-amylase, tannase and lipases such as plant lipase, gastric lipase and pancreatic lipase.

The lipase enzyme is derived from a select strain of *Aspergillus niger*, exhibiting ramdom cleaving of the 1,3 positions of fats and oils. The enzyme has maximum lipolytic activity at pH 5.0 to 7.0 when assayed with olive oil. The enzyme has a measured activity of 120,000 lipase units per gram. The lipase may be included in the dentifrice composition at a concentration of about 0.010 to about 5.0% by weight and preferably about 0.02 to about 0.10 % by weight.

The presence of tannase enzyme can be further beneficial in facilitating the breakdown of extrinsic stain. Tannase enzymes have been purified from *Aspergillus niger* and *Aspergillus allianceus* and are useful in the hydrolysis of tannins, known to discolor the tooth surface.

Other suitable enzymes which can comprise the present invention include lysozyme, derived from egg white, which contains a single polypeptide chain crosslinked by four disulfide bonds having a molecular weight of 14,600 daltons. The enzyme can exhibit antibacterial properties by facilitating the hydrolysis of bacterial cell walls cleaving the glycosidic bond between carbon number 1 of N-acetylmuramic acid and carbon number 4 of N-acetyl-D-glucosamine, which in vivo, these two corbohydrates are polymerized to form the cell wall polysaccharide. Additionally, pectinase, an enzyme that is present in most plants facilitates the hydrolysis of the polysaccharide pectin into sugars and galacturonic acid. Finally, glucanase, which may be utilized to catalyze the breakdown of complex carbohydrates to glucans and the hydrolysis of beta glucan to glucose.

Enzyme Stabilizing Agents

Enzyme stabilizing agents which protect the enzyme from inactivation by chelating metal impurities present in the oral composition include ethylene diamine tetraacetic acid (EDTA) and sodium gluconate at concentrations between 0.01 and 1% by weight, preferably between 0.1 and 0.5% by weight. Agents stabilizing the enzyme against oxidation include reducing agents such as sodium bisulfite, metal gallates, potassium stannate, sodium stannate, ammonium sulfate, 3,5,-di-tert-butyl-4-hydroxytoluene (BHT), Vitamin E ($\alpha$, $\beta$, $\gamma$, forms)/Vitamin E acetate and ascorbic acid. Potassium stannate is an enzyme stabilizing agent preferred for use in the practice of the present invention. The reducing agent is present in the oral composition of the present invention at a concentration between about 0.05 to about 1.5% by weight, preferably between about 0.1 and about 0.75% by weight.

Premix

When incorporating cetyl pyridinium chloride in the oral care composition of the present invention it is advantageous that the cetyl pyridinium chloride and any enzyme to be added to the oral composition be first premixed in an aqueous humectant solution so that the cetyl pyridinium chloride is interacted with and binds to and inactivates any impurity present in the enzyme added to the oral composition.

The premix product will normally be comprised of four components which are (1) cetyl pyridinium chloride (2) one or more enzymes to be incorporated in the oral composition (3) a reducing agent, (4) the balance, water and a humectant.

Generally the concentration of cetyl pyridinium chloride present in the premix will range from about 0.15 to about 1.0% by weight of the premix and preferably about 0.2 to about 0.6% by weight. The enzyme from about 0.5 to about 10.0% by weight of the premix and preferably about 0.75 to about 8.0% by weight. When a combination of enzymes such as glucoamylase and papain is included in the premix, the concentration of papain will range from about 2 to about 10% by weight and the concentration of glucoamylase will range from about 0.5 to about 2% by weight.

A reducing agent such as potassium stannate is also preferably included in the premix solution at a concentration of about 0.5 to about 40% by weight, and preferably about 1.0 to about 3% by weight, the presence of the reducing agent serving to further enhance the cetyl pyridinium chloride inhibition of enzyme impurity activity when subsequently incorporated in the oral composition vehicle.

Water and humectant are further components of the premix. Concentrations will range from about 85 to 95% by weight.

To prepare the premix, a reactor is charged first with a mixture of water and humectant followed by the addition of an effective amount of cetyl pyridinium chloride which is mixed and dissolved therein and thereafter the enzymes and reducing agent are added to the solution. These ingredients are mixed together at a temperature no higher than about 40° C. and preferably about 30° C. The pH is adjusted to between about 1.5 and about 8.0 and preferably from about 6.0 to about 7.5. The so prepared premix is then sealed in suitable containers waiting for blending with the vehicle and other ingredients of the oral care composition.

Oral Care Composition

In the preparation of an oral composition, the premix is mixed with the ingredients of the oral care composition vehicle to prepare a product in which the enzymes remain effectively stabilized and which will exhibit antiplaque and antigingivitis activity.

Dentifrice Vehicle

Orally-acceptable vehicles used to prepare dentifrice compositions of the present invention include a water-phase, containing a humectant therein. The humectant is preferably glycerin, sorbitol, xylitol, and/or propylene glycol of molecular weight in the range of 200 to 1,000; but, other humectants and mixtures thereof may also be employed. The humectant concentration typically totals about 5 to about 70% by weight of the oral composition and preferably about 30 to about 60% by weight. Water present in the dentifrice will range from about 10 to about 30% by weight and preferably about 15 to about 25% by weight.

Abrasives

In the preparation of a dentifrice composition, abrasives which may be used in the practice of the present invention include silica abrasives such as precipitated silicas having a mean particle size of up to about 20 microns, such as Zeodent 115, marketed by J. M. Huber. Other useful dentifrice abrasives include sodium metaphosphate, potassium metaphosphate, tricalcium phosphate, dihydrated dicalcium phosphate, aluminum silicate, calcined alumina, bentonite or other siliceous materials, or combinations thereof.

Preferred abrasive materials useful in the practice of the preparation of dentifrice compositions in accordance with the present invention include silica gels and precipitated amorphous silica having an oil absorption value of less than 100 cc/100 g silica and preferably in the range of from about 45 cc/100 g to less than about 70cc/100 g silica. Oil absorption values are measured using the ASTA Rub-Out Method D281. These silicas are colloidal particles having an average particle size ranging from about 3 microns to about 12 microns, and more preferably between about 5 to about 10 microns and a pH range from 4 to 10 preferably 6 to 9 when measured as a 5% by weight slurry.

Low oil absorption silica abrasives particularly useful in the practice of the present invention are marketed under the trade designation Sylodent XWA by Davison Chemical Division of W. R. Grace & Co., Baltimore, Md. 21203. Sylodent 650 XWA, a silica hydrogel composed of particles of colloidal silica having a water content of 29% by weight averaging from about 7 to about 10 microns in diameter, and an oil absorption of less than 70cc/100 g of silica is a preferred example of a low oil absorption silica abrasive useful in the practice of the present invention. The abrasive is present in the dentifrice composition of the present invention at a concentration of about 10 to about 40% by weight and preferably about 15 to about 30% by weight.

Thickening Agents

Thickeners used in the dentifrice compositions of the present invention include natural and synthetic gums and colloids include cellulose thickeners such as carboxymethyl cellulose, hyroxyalkyl celluloses such as hydroxypropyl cellulose hydroxyethyl cellulose, gums such as xanthan gum, polyglycols of varying molecular weights sold under the tradename Polyox and polyethylene glycol. Inorganic thickeners which may be used in the practice of the present invention include amorphous silica compounds such as colloidal silicas compounds available under the trade designation Cab-o-sil manufactured by Cabot Corporation and distributed by Lenape Chemical, Bound Brook, N.J.; Zeodent 165 from J. M. Huber Chemicals Division, Havre de Grace, Md. 21078; and Sylodent 15, available from Davison Chemical Division of W. R. Grace Corporation, Baltimore, Md. 21203. Other inorganic thickeners include natural and synthetic clays, lithium magnesium silicate (Laponite) and magnesium aluminum silicate (Veegum).

The thickening agent is present in the dentifrice composition in amounts of about 0.1 to about 10% by weight, preferably about 0.5 to about 4.0% by weight.

Surfactants

Surfactants are used in the oral compositions of the present invention to achieve increased prophylactic action and render the compositions more cosmetically acceptable. The surfactant is preferably a detersive material which imparts to the composition detersive and foaming properties.

Anionic surfactants such as higher alkyl sulfates such as sodium lauryl sulfate are effective surfactants in oral compositions but are normally not compatible with enzymes and promote denaturation of the enzyme and loss in activity. However, in accordance with the practice of the present invention, premixing concentrated amounts of enzymes such as glucoamylase with cetyl pyridinium chloride, allows the cetyl pyridinium chloride to interact and bind to any cellulase impurity present in the glucoamylase thereby preventing interaction of the cellulase with any cellulose based thickener that may be used in preparing the dentifrice as well as inhibiting interaction with the anionic surfactant. Surfactants that are compatible with enzymes may also be used to provide the requisite foaming characteristics in the oral composition. Examples of enzyme compatible surfactants include nonionic polyoxyethylene surfactants such as Polyoxamer 407, Pluronic 127, Polysorbate 20, and amphoteric surfactants such as tauranol, cocamidopropyl betaine (tegobetaine) and cocamidopropyl betaine lauryl glucoside. Surfactants are included in the oral composition of the present invention at a concentration of about 2 to about 10% by weight and preferably between about 0.5 to about 5.0% by weight.

Fluoride and Other Active Agents

The oral composition of the present invention may also contain a source of fluoride ions or fluorine-providing ingredient, as anticaries agent in amounts sufficient to supply about 25 ppm to 5,000 ppm of fluoride ions and include inorganic fluoride salts, such as soluble alkali metal salts. Preferred fluoride sources which are compatible with enzymes include sodium fluoride, potassium fluoride, sodium fluorosilicate, sodium monfluorophosphate (MFP), ammonium fluorosilicate, as well as tin fluorides, such as stannous fluoride and stannous chloride. Sodium fluoride or MFP is preferred.

In addition to fluoride compounds, there may also be included in the oral compositions of the present inventions antitartar agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, polyphosphates such as sodium tripolyphosphate, sodium hexametaphosphate and cyclic phosphates such as sodium tripolyphosphate sodium trimetaphosphate. These antitartar agents are included in the dentifrice composition at a concentration of about 1.0 to about 5.0% by weight.

Another active agent useful in dentifrice compositions of the present invention are antibacterial agents, which can be from 0.2 to 1.0% by weight of the oral composition. Such useful antibacterial agents include non-cationic antibacterial agents which are based on phenolic or bisphenolic compounds, such as halogenated diphenyl ethers such as Triclosan (2,4,4'-trichloro-2'-hydroxydiphenyl ether).

Anionic Polycarboxylate

Synthetic anionic polycarboxylates may also be used in the oral compositions of the present invention as an efficacy enhancing agent for any antibacterial, antitartar or other active agent within the dentifrice composition. Such anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of about 30,000 to about 1,800,000 most preferably about 30,000 to about 700,000. Examples of these copolymers are available from GAF Corporation under the tradename Gantrez, e.g. AN 139 (M.W. 500,000), AN 119 (M.W. 250,000); S-97 Pharmaceutical Grade (M.W. 700,000), AN 169 (M.W. 1,200,000–1,800,000), and AN 179 (M.W. above 1,800,000); wherein the preferred copolymer is S-97 Pharmaceutical Grade (M.W. 700,000).

When present, the anionic polycarboxylates is employed in amounts effective to achieve the desired enhancement of the efficacy of any antibacterial, antitartar or other active agent within the oral composition. Generally, the anionic polycarboxylates is present within the oral composition from about 0.05% to about 4% by weight, preferably from about 0.5% to about 2.5% by weight.

Flavor

The oral composition of the present invention may also contain a flavoring agent. Flavoring agents which are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint.

The flavoring agent is incorporated in the oral composition at a concentration of about 0.1 to about 5% by weight and preferably about 0.5 to about 1.5% by weight.

Other Ingredients

Various other materials may be incorporated in the oral compositions of this invention, including desensitizers, such as potassium nitrate; whitening agents, such as hydrogen peroxide, calcium peroxide and urea peroxide; preservatives; silicones; and chlorophyll compounds. These additives, when present, are incorporated in the oral compositions of the present invention in amounts which do not substantially adversely affect the properties and characteristics desired.

Preparation of Dentifrice Compositions

To prepare a dentifrice composition of the present invention, generally the humectants such as glycerin, sorbitol are dispersed in the water in a conventional mixer under agitation. Into the dispersion are added organic thickeners, such as carboxymethyl cellulose; antitartar agents such as tetrasodium pyrophosphate, sodium tripolyphosphate and any sweeteners. The resultant mixture is agitated until a homogeneous gel phase is formed. Into the gel phase are added a pigment such as $TiO_2$, and any acid or base required to adjust the pH in the range of 6.4 to 7.3. These ingredients are mixed until a homogenous phase is obtained. Thereafter a premix of cetyl pyridinium chloride, enzyme and a reducing agent such as potassium stannate in an aqueous humectant solution is added and admixed with the homogeneous gel phase The resultant mixture is then transferred to a high speed/vacuum mixer; wherein, the thickener, and surfactant ingredients are added to the mixture. Thereafter the abrasive is added. Any water insoluble antibacterial agent, such as Triclosan, is solubilized in the flavor oils to be included in the composition and the solution is added along with the surfactants to the mixture, which is then mixed at high speed for from 5 to 30 minutes, under vacuum of from about 20 to 50 mm of Hg, preferably about 30 mm Hg. The resultant product is in each case a homogeneous, semi-solid, extrudable paste or gel product.

Preparation of Liquid Oral Compositions

In the aspect of the present invention wherein the oral composition is substantially liquid in character such as a mouthwash or rinse, the vehicle is typically a water, humectant, alcohol mixture. The alcohol is a non-toxic alcohol such as ethanol or isopropanol. A humectant such as glycerine, sorbitol or an alkylene glycol such as polyethylene glycol or propylene glycol may be present in an amount of about 10 to 30% by weight, the oral rinse containing greater than about 45% by weight water and preferably about 50 to 85% by weight water, about 0 to 20% by weight of a non-toxic alcohol and about 10 to 40% by weight of the humectant. A thickener such as a Pluronic may be present at a concentration of about 1.0 to about 3.0% by weight, cetyl pyridinium chloride at a concentration of about 0.02 to about 1.0% by weight, a reducing agent such potassium stannate or ammonium sulfate at a concentration of about 0.05 to 1.0% by weight, an enzyme at a concentration of about 0.02 to about 0.2 % by weight and a flavor ingredient at a concentration of about 0.3 to about 1.0 % by weight.

In the preparation of a oral rinse, an enzyme premix comprised of cetyl pyridinium chloride, reducing agent, water, humectant and enzyme is dispersed in a mixture of mouthwash ingredients, for example, alcohol, humectants, surfactants, and flavor are then added and mixed. The ingredients are then mixed under vacuum for about 15–30 minutes. The resulting oral rinse product is then packaged.

A rinse is an advantageous vehicle for delivering actives to the oral cavity, due to its ability to get into hard-to-reach areas of the mouth, such as the interproximal regions and the crevices of the tongue. The challenge in incorporating enzymes into a rinse is maintaining enzymatic stability and activity at water levels above 50%, conventionally not suitable for enzyme containing compositions. In the present invention, the stability of enzyme activity is found to be acceptable and is optimized unexpectedly when the water content of the rinse is maintained above 45% by weight of a mixture thereof, and preferably about 50 to about 85% by weight enzyme activity as an antiplaque agent is found to increase as will hereinafter be demonstrated.

The following examples further describe and demonstrate preferred embodiments within the scope of the present invention. The examples are given solely for illustration, and are not to be construed as a limitation of this invention as many variations thereof are possible without departing from its spirit and scope.

EXAMPLE I

An enzyme (papain, glucoamylase) containing dentifrice composition containing a small but effective amount of cetyl pyridinium chloride and reducing agents (potassium stannate, ammonium sulfate) added as enzyme premix and thickened with a cellulose thickener (carboxymethyl cellulose) was prepared. The ingredients of this composition designated, "Composition A", are listed in Table I below.

Dentifrice compositions designated Compositions "B, C and D" were prepared following the procedure of Example I for the purpose of comparison. All the compositions contained the same enzymes as Composition A namely, glucoamylase and papain. Compositions B and C did not contain cetyl pyridinium chloride.

Composition B contained the reducing agent ammonium sulfate and the metal chelating agent EDTA. Composition C contained the reducing agent potassium stannate and the preservative Nipastat. Composition D contained cetyl pyridinium chloride in the dentifrice composition base and did not contain a reducing agent and Laponite was substituted for sodium carboxymethyl cellulose as a thickening agent.

Commercial dental cream that did not contain cetyl pyridinium chloride or enzymes designated "Composition E" was used as a control.

TABLE I

| Composition Ingredients | A Wt. % | B Wt. % | C Wt. % | D Wt. % |
| --- | --- | --- | --- | --- |
| Water | 18.25 | 17.75 | 18.25 | 18.25 |
| Pluronic F127 | 1.5 | 1.5 | 1.5 | 0.75 |
| Glycerin | 20.0 | 20.0 | 20.0 | 22.0 |
| Tetrasodium pyrophosphate | 2.0 | 2.0 | 2.0 | — |
| Sodium tripolyphosphate | 3.0 | 3.0 | 3.0 | — |
| Monosodium phosphate | 0.026 | 0.026 | 0.026 | — |
| Disodium phosphate | 0.079 | 0.079 | 0.079 | — |
| Sodium carboxymethyl cellulose | 0.65 | 0.65 | 0.65 | — |
| Laponite | — | — | — | 0.7 |
| Xanthan gum | 0.55 | 0.55 | 0.55 | 0.6 |
| Sodium monofluoro phosphate | 0.76 | 0.76 | 0.76 | 0.76 |
| Sodium saccharin | 0.50 | 0.50 | 0.50 | 0.40 |
| Sorbitol (70% solution) | 18.9434 | 19.6999 | 19.2024 | 22.8049 |
| Silica XWA650 | 20.0 | 20.0 | 20.0 | 20.0 |
| Zeodent 115 | 5.0 | 5.0 | 5.0 | 5.0 |
| Zeodent 165 | 2.25 | 2.0 | 2.0 | 2.25 |
| Titanium dioxide | 0.40 | 0.40 | 0.40 | 0.50 |
| Sodium lauryl sulfate | 0.50 | 0.50 | 0.50 | — |

TABLE I-continued

| Composition Ingredients | A Wt. % | B Wt. % | C Wt. % | D Wt. % |
|---|---|---|---|---|
| Tauranol | — | — | — | 1.2 |
| Betaine | 1.0 | 1.0 | 1.0 | — |
| PEG 600 | 3.0 | 3.0 | 3.0 | 3.0 |
| Polyoxomer 407 | 0.10 | 0.10 | 0.10 | 0.10 |
| Flavor | 1.10 | 1.10 | 1.10 | 1.10 |
| Papain | 0.2266 | 0.2266 | 0.2266 | 0.2266 |
| Glucoamylase | 0.044 | 0.044 | 0.044 | 0.044 |
| Potassium stannate | 0.10 | — | 0.10 | — |
| Ammonium sulfate | — | 0.10 | — | — |
| Cetyl pyridinium chloride | 0.015 | — | — | 0.3 |
| EDTA, disodium dihydrate | 0.006 | 0.006 | 0.006 | 0.006 |
| Nipastat | — | — | 0.006 | — |
| Sodium benzoate | — | 0.0025 | — | 0.0025 |
| Potassium sorbate | — | 0.006 | — | 0.006 |

Premixes designated B1, C1 and D1 were prepared following the procedure used for Premix A1 and added to respective dentifrice Compositions B, C and D. The ingredients used in the preparation of the premix compositions for Compositions A, B, C, D are listed in Table II below.

TABLE II

| Composition Ingredients | Premix Ingredients | | | |
|---|---|---|---|---|
|  | A1 Wt. % | B1 Wt. % | C1 Wt. % | D1 Wt. % |
| Sorbitol | 67.168 | 76.848 | 67.348 | 76.848 |
| Water | 25 | 15 | 25 | 15 |
| Papain | 4.532 | 4.532 | 4.532 | 4.532 |
| Glucoamylase | 0.88 | 0.88 | 0.88 | 0.88 |
| Potassium stannate | 2.0 | — | 2.0 | 2.0 |
| Ammonium sulfate | — | 2.0 | — | — |
| cetyl pyridinium chloride | 0.3 | — | — | — |
| EDTA, disodium dihydrate | 0.12 | 0.12 | 0.12 | 0.12 |
| Nipastat | — | — | 0.12 | — |
| Sodium benzoate | — | 0.5 | — | 0.5 |
| Potassium sorbate | — | 0.12 | — | 0.12 |

Premix compositions A1, B1, C1 and D1 were separately added to a non-enzyme dental cream containing the ingredients listed in Table I in a 1:4 ratio to observe the effects on cellulase activity. Cellulase activity was monitored via both viscosity and sugar level changes in Dentifrice Compositions A, B, C and D over time.

In viscosity measurements, greater cellulase activity was discernible by a more rapid reduction in toothpaste viscosity as the cellulase catabolized the carboxymethyl cellulose thickener used to prepare the dentifrice compositions. Brookfield model RVDTV-11 viscometer with spindle #95 at 5 rpm measured viscosity in centipose per second$_2$ (CPS). Measurements were taken daily of each sample until an 80% loss in viscosity was observed.

The sugar byproduct concentration was monitored using an Accucheck blood sugar digital analyzer. As cellulase acts upon cellulose, sugar is produced as a byproduct. The greater the amount of cellulase activity, the greater the amount of sugar produced. Both the sugar level and viscosity methods were used to compare the effects of cetyl pyridinium chloride, the reducing agents ammonium sulfate and potassium stannate and preservative agents sodium benzoate, and parabens on cellulase activity. The viscosity and sugar concentration results are recorded in Table m below.

TABLE III

| Composition Ingredients | Initial Viscosity (CPS) | Final Viscosity (CPS) | % Viscosity Loss (After 14 Days) | Sugar Conc. (MG/DL) (After 7 Days) |
|---|---|---|---|---|
| A | 25 | 17 | 32 | 28 |
| B | 20 | 10 | 50 | 62 |
| C | 20 | 5 | 75 | 62 |
| D | 30 | 15 | 50 | 62 |
| E | 28 | 32 | 0 | 0 |

The results in Table III show that the trend in sugar production is consistent with the viscosity loss results. Both tests indicate that Composition A formulated with a potassium stannate/cetyl pyridinium chloride/enzyme premix solution was most effective in delaying cellulase activity upon the dentifrice composition.

Tongue Microflora Reduction

Several compositions were tested for tongue microflora reduction, focussing on those species responsible for the generation of oral malodor. Patients swabbed the tongue for bacterial collection at baseline and four hours post treatment. These samples were plated onto agar media and incubated anaerobically. After four days, colony forming units of malodor causing bacteria and also total tongue bacteria were enumerated. The average colony forming unit results were used to calculate percent reduction from baseline.

Table IV and V represents in-vivo tongue microflora study with bacterial sampling at baseline and at four hours post-brushing with Composition D. For purposes of comparison Compositions F and G were also evaluated for oral malodor and tongue microflora reduction. Composition F was a commercial dentifrice which contained cetyl pyridinium chloride but no enzymes and compositions G was a commercial fluoride toothpaste which did not contain cetyl pyridinium chloride enzymes. Table V shows the increased reduction of oral malodor causing bacteria by the combination of enzymes with cetyl pyridinium chloride present in Composition D. Table VI demonstrates that this stabilized enzyme premix when incorporated into toothpaste systems provides an in-vivo antibacterial effect against all types of bacteria that exist on the tongue, including the malodor causing species. After four hours post treatment Formulation D, containing cetyl pyridinium chloride and enzymes significantly reduced more bacteria than the comparative dentifrices F and G.

TABLE IV

Reduction of malodor tongue bacteria 4 hours post treatment

| Composition | Baseline Mean colonies | After 4 hours Mean colonies | % Reduction of Malodor Bacteria Colonies |
|---|---|---|---|
| D | $3.8 * 10^5$ | $1.4 * 10^5$ | 63 |
| F | $2.3 * 10^5$ | $2.3 * 10^5$ | 0 |
| G | $2.0 * 10^5$ | $2.3 * 10^5$ | 0 |

TABLE V

Reduction of total tongue bacteria 4 hours post treatment

| Composition | Baseline Mean colonies | After 4 hours Mean colonies | % Reduction of Malodor Bacteria Colonies |
|---|---|---|---|
| D | $5.2 * 10^5$ | $2.4 * 10^5$ | 53 |
| F | $5.0 * 10^5$ | $3.1 * 10^5$ | 38 |
| G | $4.3 * 10^5$ | $3.9 * 10^5$ | 10 |

EXAMPLE II

Oral rinses designated "Compositions K and L" were prepared having the ingredients listed in Table VI below.

TABLE VI

| Composition Ingredients | K (Wt. %) | L (Wt. %) |
|---|---|---|
| Water | 57.8 | 70.3 |
| Glycerin | 16.25 | 10.0 |
| Sorbitol | 16.25 | 10.0 |
| Ethanol | 5.00 | 5.00 |
| Gantrez | 1.92 | 1.92 |
| Pluronic F127 | 0.75 | 0.75 |
| Pluronic F108 | 0.75 | 0.75 |
| Tetrasodium pyrophosphate | 0.45 | 0.45 |
| Flavor | 0.30 | 0.30 |
| Papain | 0.21 | 0.21 |
| Potassium stannate | 0.05 | 0.05 |
| Sodium saccharin | 0.070 | 0.070 |
| Cetylpyridinium chloride | 0.050 | 0.050 |
| Nipastat | 0.050 | 0.050 |
| Monosodium phosphate | 0.035 | 0.035 |
| Butyl hydroxy toluene | 0.015 | 0.015 |
| Disodium phosphate | 0.010 | 0.010 |
| Phosphoric acid | 0.04 | 0.04 |
| Total | 100.0 | 100.0 |

Papain Stability

The papain activity of the rinse was monitored using the PanVera Protease Activity Kit. The activity kit quantifies protease activity using a fluorescein thiocarbamoyl (FTC)-casein substrate. FTC-casein is attacked by the protease, breaking down casein into TC-peptides. The amount of protease activity is determined by measuring the fluorescence of the FTC peptides generated. Table VII below compares the percent activity and fluorescence of Compositions K and L, and a placebo designated "Composition N" which is identical to Composition K, but does not contain enzymes. Fluorescence values are expressed in relative fluorescene units, RFU's Percent activity is determined from the fluorescence, relative to the placebo. From activity measurements above 70% of the enzyme activity was maintained after 4 weeks at room temperature.

TABLE VII

PROTEASE ACTIVITY

| Oral Rinse | Initial Florescence(RFU) | After 4 Weeks Fluorescence(RFU) | % Reduction |
|---|---|---|---|
| K | 25983 | 21518 | 74% |
| L | 26548 | 21297 | 72% |
| N | 10360 | 11563 | 0 |

Plaque Removal Efficacy

To evaluate the plaque removal ability of the papain enzyme rinse Compositions K and L, a salivary flow cell study was performed in which plaque was grown onto a model surface, followed by treating the surface with a rinse and measuring the reduction of plaque. In the study, a plaque biofilm was first formed onto germanium prisms by continuously pumping bacteria growth media over the prisms for approximately 18 hours. Next, the prisms were treated with a rinse composition, pumping rinse over the prisms for several minutes, in order to facilitate plaque removal. A plaque index was calculated, using Attenuated Total Reflection Fourier Transform Infrared spectroscopy (ATR FTIR) absorption band intensities at 3300, 1650, 1545 and 1080 $cm^{-1}$ from the infrared spectrum as follows:

$$\text{Plaque Score} = abs_{3300} + abs_{1650} + abs_{1545} + abs_{1080}$$

where abs is the maximum absorbance at the various wave numbers. The wave numbers selected represent the infrared adsorption by salivary components and bacteria on the infrared-transparent germanium prisms. The plaque index of the rinse treated prisms were then compared to a baseline (prism rinsed with saline only), and reported as percent plaque reduction.

The results recorded in Table IX below, compares the plaque reduction performance of oral rinse Compositions K and L of the present invention versus a commercial rinse designated Composition M which contained 0.05% by weight cetyl pyridinium chloride but no enzymes and the placebo designated "Composition N". The percent plaque reduction of the high water containing rinse, rinse L was 17% better than rinse K. The results indicate that there is greater improvement in the delivery of actives to the plaque surface with the high water, less viscous formula although both rinses were effective to reduce plaque to a greater degree than the commercial rinse Composition M when compared to the placebo Composition N.

The results are recorded in Table IX below.

TABLE IX

| Composition | Plaque Index | % Plaque Reduction |
|---|---|---|
| K | 2.320 | 20 |
| L | 1.832 | 37 |
| M | 2.864 | 1 |
| N | 2.529 | 13 |
| Rinsed with saline solution only | 2.901 | — |

Inhibition of Plaque Formation

The ability of the enzyme rinse to inhibit plaque formation was evaluated using the salivary flow cell wherein the study was performed in a similar manner as described above for plaque removal, except that the germanium prisms are pretreated with the rinse for several minutes, followed by an 18 hour post treatment with bacterial growth media to facilitate growth of a plaque biofilm onto the prism surface. The amount of plaque formed (plaque index) on the prisms was again determined by measuring the total amide absorption by ATR FTIR. The plaque index of the rinse treated prisms is compared to a placebo, Composition N and expressed as percent plaque inhibition.

Table X compares the percent plaque inhibition of rinses K and L relative to the commercial rinse M containing cetyl pyridinium chloride but no enzymes, and the placebo N which was identical to Composition K except it did not contain enzymes. The results recorded in Table X indicate that the lower water, more viscous rinse Composition K is more effective in coating the plaque free surface, forming a greater protective barrier for inhibiting plaque formation than Composition L.

TABLE X

| Oral Rinse | Plaque Index | % Plaque Inhibition |
|---|---|---|
| K | 0.683 | 35 |
| L | 0.801 | 24 |
| M | 0.968 | 8 |
| N | 1.053 | — |

Intradental Plaque Removal

The propensity of the enzyme rinse to remove intradental plaque was demonstrated using an in vitro cleaning model. The model involved pretreating dentures with the rinse, growing plaque onto the denture surface, followed by post-treatment of the dentures with the rinse. In this model, removable dentures were first pumiced, rinsed with water, and sterilized with ethanol for 10 minutes in a trough of a brushing machine, in order to provide a clean denture surface. Next the dentures are submersed in a rinse solution, and incubated overnight at room temperature. Following overnight treatment, the dentures are rinsed with water and submersed into bacterial growth media for 6 hours at 37° C. Finally, the models were rinsed briefly with water, followed by brief rinsing with mouth rinse formulas. The dentures were then disclosed with disclosing solution for 30 seconds, rinsed briefly with water, and then rated with a plaque score determined using the Quigley Hein Plaque method.

The high water containing rinse, Composition L was tested in the in vitro cleaning model. Results recorded in Table XI indicate, that in comparison the commercial rinse M containing cetyl pyridinium chloride but no enzymes and the placebo rinse N, the enzyme rinse L significantly reduced both total and interproximal plaque by 67% demonstrating Composition L not only effectively reduces approximal plaque, but is also effective in cleaning in interproximal regions, demonstrating a "floss type" action.

TABLE XI

| INTRADENTAL PLAQUE | | | | |
|---|---|---|---|---|
| Oral Rinse | Plaque Index (Interproximal) | Plaque Index (Total) | % Total Plaque Reduction | % Interproximal Plaque Reduction |
| L | 1.00 | 1.50 | 67 | 67 |
| M | 3.00 | 4.58 | — | — |
| N | 3.00 | 4.58 | — | — |

What is claimed is:

1. An oral care composition having enhanced stability and antiplaque effectiveness which comprises an orally acceptable vehicle which is a dentifrice containing an enzyme which can often contain cellulose, an undesirable, difficult to remove impurity, which degrades cellulose and cellulose polymer thickeners, said dentifrice thickened with a cellulose polymer containing a combination of said enzyme, cetyl pyridinium chloride and a reducing agent.

2. The composition of claim 1 wherein the enzyme is a proteolytic enzyme.

3. The composition of claim 2 wherein the proteolytic enzyme is papain.

4. The composition of claim 3 wherein the papain is present in the composition at a concentration of about 0.1 to about 5.0% by weight of the composition.

5. The composition of claim 1 wherein the enzyme is glucoamylase.

6. The composition of claim 1 wherein the glucoamylase is present in the oral composition at a concentration of about 0.1 to 5.0% by weight.

7. The composition of claim 2 wherein the cetyl pyridinium chloride is present in the composition at a concentration of about 0.005 to about 2% by weight.

8. The composition of claim 1 wherein the reducing agent is potassium stannate.

9. The composition of claim 2 wherein the reducing agent is ammonium sulfate.

10. The composition of claim 1 wherein the reducing agent is present in the composition at a concentration of about 0.05 to about 2.0% by weight of the composition.

11. The composition of claim 1 wherein the composition is a dentifrice thickened with a cellulose polymer.

12. The composition of claim 11 wherein the cellulose polymer is carboxymethyl cellulose.

13. A method for effecting enhanced stability in an oral composition containing enzymes which comprises preparing a composition comprised of an orally acceptable vehicle which is a dentifrice containing an enzyme which can often contain cellulose, an undesirable, difficult to remove impurity, which degrades cellulose and cellulose polymer thickeners, said dentifrice thickened with a cellulose polymer containing a combination of said enzyme, cetyl pyridinium chloride and a reducing agent and then applying the composition to the oral cavity.

14. The method of claim 13 wherein the enzyme is a proteolytic enzyme.

15. The method of claim 13 wherein proteolytic enzyme is papain.

16. The method of claim 15 wherein the papain is present in the composition at a concentration of about 0.1 to about 5.0% by weight of the composition.

17. The method of claim 13 wherein the enzyme is glucoamylase.

18. The method of claim 17 wherein the glucoamylase is present in the oral composition at a concentration of 0.1 to 5.0% by weight.

19. The method of claim 13 wherein the enzyme is incorporated in the composition as an aqueous dispersion of a papain and glucoamylase.

20. The method of claim 13 wherein the reducing agent is potassium stannate.

21. The method of claim 13 wherein the reducing agent is ammonium sulfates.

22. The method of claim 13 wherein the reducing agent is present in the composition at a concentration of about 0.05 to about 2.0% by weight of the composition.

23. The method of claim 13 wherein the composition is a dentifrice thickened with a cellulose polymer.

24. The method of claim 13 wherein the cellulose polymer is carboxymethyl cellulose.

25. The method of claim 13 wherein the cetyl pyridinium chloride is present in the composition at a concentration of about 0.005 to about 2% by weight.

26. A method for the preparation of an aqueous oral care composition containing a stable enzyme compound which comprises first dissolving the enzyme in an aqueous solution of cetyl pyridinium chloride and a reducing agent or to prepare a premix and then adding the premix to the vehicle which is a dentifrice containing an enzyme which can often contain cellulose, an undesirable, difficult to remove impurity, which degrades cellulose and cellulose polymer thickeners, said dentifrice thickened with a cellulose polymer of the oral care composition.

27. The method of claim 26 wherein the enzyme is present in the premix at a concentration of about 0.1 to about 10% by weight.

28. The method of claim 26 wherein the enzyme is glucoamylase.

29. The method of claim 26 wherein the reducing agent is present in the oral care composition at a concentration of about 0.05 to about 3% by weight.

30. The method of claim 26 wherein the enzyme is papain.

* * * * *

UNITED STATES PATENT AND TRADEMARK OFFICE
CERTIFICATE OF CORRECTION

PATENT NO.    : 6,692,726 B1
DATED         : February 17, 2004
INVENTOR(S)   : Andrè M. Morgan et al.

It is certified that error appears in the above-identified patent and that said Letters Patent is hereby corrected as shown below:

Column 13,
Line 56, "cellulose" should be -- cellulase --

Column 14,
Lines 23 and 64, "cellulose" should be -- cellulase --

Signed and Sealed this

Twelfth Day of October, 2004

JON W. DUDAS
*Director of the United States Patent and Trademark Office*